US005422252A

United States Patent [19]
Walker et al.

[11] Patent Number: 5,422,252
[45] Date of Patent: Jun. 6, 1995

[54] SIMULTANEOUS AMPLIFICATION OF MULTIPLE TARGETS

[75] Inventors: George T. Walker; James G. Nadeau, both of Chapel Hill; Michael C. Little, Raleigh, all of N.C.

[73] Assignee: Becton, Dickinson and Company, Franklin Lakes, N.J.

[21] Appl. No.: 73,197

[22] Filed: Jun. 4, 1993

[51] Int. Cl.[6] ............... C12P 19/34; C12Q 1/70
[52] U.S. Cl. .................... 435/91.2; 435/6; 935/17; 935/77; 935/78
[58] Field of Search ........... 435/6, 5, 91.2; 935/77, 935/78, 17

[56] References Cited

U.S. PATENT DOCUMENTS

| | | | |
|---|---|---|---|
| 4,683,195 | 7/1987 | Mullis | 435/6 |
| 4,683,202 | 7/1987 | Mullis | 435/91 |
| 4,800,159 | 1/1989 | Mullis et al. | 435/172.3 |
| 5,104,792 | 4/1992 | Silver | 435/6 |

FOREIGN PATENT DOCUMENTS

| | | |
|---|---|---|
| 0356021 | 2/1990 | European Pat. Off. . |
| 0364255 | 4/1990 | European Pat. Off. . |
| 0379369 | 7/1990 | European Pat. Off. . |
| 0469755 | 2/1992 | European Pat. Off. . |
| WO90/01064 | 2/1990 | WIPO . |
| WO90/09457 | 8/1990 | WIPO . |

OTHER PUBLICATIONS

Bej, Critical Reviews in Biochem. Molec. Biol. 26:301–334 (1991).
Fries et al Molec. and Cell Probes (1990) 4:87–105.
G. T. Walker, et al. "Isothermal in vitro amplification of DNA by a restriction enzyme/DNA polymerase system" Proc. Acad. Sci. USA 89:392–396 (1992).
G. T. Walker, et al. "Strand displacement amplification—an isothermal, in vitro DNA amplification technique" Nuc. Acids Res. 20:1691–1696 (1992).
P. R. Mueller and B. Wold "In Vivo Footprinting of a Muscle Specific Enhancer by Ligation Mediated PCR" Science 246:780–786 (1989).
V. Shyamala and G. F.-L. Ames "Genome walking by single-specific-primer polymerase chain reaction: SSP-PCR" Gene 84:1–8 (1989).
A. R. Shuldiner, et al. "RNA template-specific polymerase chain reaction (RS-PCR): a novel strategy to reduce dramatically false positives" Gene 91:139–142 (1990).
D. H. Jones and S, C. Winistorfer "Sequence specific generation of a DNA panhandle permits PCR amplification of unknown flanking DNA" Nuc. Acids Res. 20:595–600 (1992).
K. D. Eisenach, et al. "Detection of *Mycobacterium tuberculosis* in Sputum Samples Using a Polymerase Chain Reaction" Amer. Rev. Resp. Dis. 144:1160–1163 (1991).

Primary Examiner—Margaret Parr
Assistant Examiner—Carla Myers
Attorney, Agent, or Firm—Donna R. Fugit

[57] ABSTRACT

Methods for multiplex amplification of target nucleic acid sequences using a single pair of primers. Defined sequences are appended to the ends of multiple target sequences as part of the amplification reaction so that no steps in addition to amplification are required. The target sequences with the appended defined sequences need not be isolated prior to amplification. In one embodiment for coamplification of two target sequences, a sequence corresponding to a terminal segment of the first target sequence is appended to one end of the second target sequence and a sequence corresponding to a terminal segment of the second target sequence is appended to one end of the first target sequence. Amplification of the two targets then requires only a single pair of primers. Alternatively, a single defined sequence may be appended to the 5' and 3' ends of any number of selected targets. All such modified target sequences may then be amplified using a single pair of primers which hybridize to the defined end-sequences.

17 Claims, 5 Drawing Sheets

SIMULTANEOUS AMPLIFICATION OF MULTIPLE TARGETS

FIELD OF THE INVENTION

The present invention relates to isothermal amplification of nucleic acid target sequences, in particular to simultaneous amplification of multiple target sequences.

BACKGROUND OF THE INVENTION

In vitro nucleic acid amplification techniques have provided powerful tools for detection and analysis of small amounts of nucleic acids. The extreme sensitivity of such methods has lead to attempts to develop them for diagnosis of infectious and genetic diseases, isolation of genes for analysis, and detection of specific nucleic acids as in forensic medicine. Nucleic acid amplification techniques can be grouped according to the temperature requirements of the procedure. The polymerase chain reaction (PCR; R. K. Saiki, et al. 1985. *Science* 230, 1350–1354), ligase chain reaction (LCR; D. Y. Wu, et al. 1989. *Genomics* 4, 560–569; K. Barringer, et al. 1990. *Gene* 89, 117–122; F. Barany. 1991. *Proc. Natl. Acad. Sci. USA* 88, 189–193) and transcription-based amplification (D. Y. Kwoh, et al. 1989. *Proc. Natl. Acad. Sci. USA* 86, 1173–1177) require temperature cycling. In contrast, methods such as strand displacement amplification (SDA; G. T. Walker, et al. 1992. *Proc. Natl. Acad. Sci. USA* 89, 392–396; G. T. Walker, et al. 1992. *Nuc. Acids. Res.* 20, 1691–1696), selfsustained sequence replication (3SR; J. C. Guatelli, et al. 1990. *Proc. Natl. Acad. Sci. USA* 87, 1874–1878) and the Qβ replicase system (P. M. Lizardi, et al. 1988. *BioTechnology* 6, 1197–1202) are isothermal reactions. In addition, WO 90/10064 and WO 91/03573 describe use of the bacteriophage phi29 replication origin for isothermal replication of nucleic acids.

In general, diagnosis and screening for specific nucleic acids using nucleic acid amplification techniques has been limited by the necessity of amplifying a single target sequence at a time. In instances where any of multiple possible nucleic acid sequences may be present (e.g., infectious disease diagnosis), performing multiple separate assays by this procedure is cumbersome and time-consuming. U.S. Pat. Nos. 4,683,195; 4,683,202 and 4,800,159 describe the PCR. Although these inventors state that multiple sequences may be detected, no procedure for amplifying multiple target sequences simultaneously is disclosed. When multiple target sequences are amplified, it is by sequentially amplifying single targets in separate PCRs. In fact, when multiple pairs of primers directed to different target sequences are added to a single PCR, the reaction produces unacceptably high levels of nonspecific amplification and background. An improvement on the PCR which reportedly allows simultaneous amplification of multiple target sequences is described in published European Patent Application No. 0 364 255. This is referred to as multiplex DNA amplification. In this method, multiple pairs of primers are added to the nucleic acid containing the target sequences. Each primer pair hybridizes to a different selected target sequence, which is subsequently amplified in a temperature-cycling reaction similar to PCR.

Certain nucleic acid amplification procedures have employed addition of defined sequences to the ends of nucleic acid fragments prior to amplification. U.S. Pat. No. 5,104,792 describes a modification of PCR which allows amplification of nucleic acid fragments for which the sequence is not known. The primers for the amplification reaction contain random degenerate sequences at their 3' ends and a defined sequence at their 5' ends. Extension of the primers produces fragments containing unknown sequences which are flanked by the defined sequence. These fragments may then be amplified in a conventional PCR using primers which hybridize to the known flanking sequence. Another method for PCR amplification of unknown DNA which flanks a known sequence is described by D. H. Jones and S. C. Winistorfer (1992. *Nuc. Acids. Res.* 20, 595–600, "panhandle PCR"). In panhandle PCR, a single-stranded oligonucleotide complementary to a sequence in the known DNA is ligated to the 3' ends of a double stranded fragment. Upon denaturation and intrastrand reannealing, the complementary sequences hybridize and the recessed 3' end is extended with polymerase, producing the unknown sequence flanked by the known sequence. The known sequence can then be used to prepare primers for amplification of the unknown sequence. Similar methods for generation of a hairpin structure and single primer amplification are described in published European Patent Application No. 0 379 369. WO 90/09457 describes a sequence-independent method for amplification of DNA sequences which are entirely unknown. Universal oligonucleotide primer pairs are ligated to the target DNA by blunt-end ligation so that PCR amplification may be primed using these known primers.

Several methods are known which allow amplification of target sequences when only partial sequence information is known. A. R. Shuldiner, et al. (1990. *Gene* 91, 139–142) describe a modification of reverse transcription PCR in which a unique sequence is appended to the 5' end of the first strand during reverse transcription. First strand synthesis is primed by a hybrid primer which is complementary to the RNA target at the 3' end and contains the unique sequence at the 5' end. The cDNA is then amplified using a primer directed to the unique sequence and a primer directed to a target-specific sequence. This reportedly reduces amplification of carryover contaminants. Published European Patent Application No. 0 469 755 discloses a method for producing single stranded polynucleotides having two segments that are non-contiguous and complementary. A sequence complementary to an existing sequence in the polynucleotide is introduced by extension of a primer which hybridizes to the polynucleotide at its 3' end and has the complement of the existing sequence at its 5' end. After extension of the primer the polynucleotide can be amplified using a single primer. V. Shyamala and G. F. L. Ames (1989. *Gene* 84, 1–8) teach a method for PCR amplification of DNA when the sequence of only one end is available (SSP-PCR). The unknown end is ligated to a genetic vector sequence, and the fragment is amplified using a gene-specific primer and a generic vector primer. Similar methods are disclosed in Published European Patent Application No. 0 356 021. WO 90/01064 describes amplification of a sequence by synthesizing a complementary strand primed with a sequence-specific primer directed to a known portion of the sequence. A homopolymer is added to the 3' end of the complement and the sequence is amplified using a homopolymer primer and a primer which is homologous to a region of the sequence-specific primer. Adaptation of PCR to footprinting is taught by P. R. Mueller and B. Wold (1989. *Science* 246, 780–786). For footprinting, a common oligonucleotide sequence is ligated to the unique end of each fragment of the footprint ladder. The fragments are amplified using a primer complementary to the common sequence and a primer complementary to the known sequence of the fixed end.

The present methods provide a means for appending any adapter sequence or any pair of adapter sequences to any target prior to amplification by primer extension. The adapter sequences reduce the number of specific primers which are required for simultaneous amplification of two or more target sequences in a single primer extension amplification reaction (referred to herein as "multiplex amplification" or "multiplexing"). Conventional multiplexing involves putting into the reaction primers specific for amplification of each target sequence, i.e., each target is amplified by a specific primer or pair of primers. Conventional multiplexing provides satisfactory results in certain circumstances, but has drawbacks in that multiple specific primers must be prepared for each multiplex reaction. Often, however, multiple sequences cannot be readily amplified and detected using conventional multiplexing due to generation of high levels of nonspecific background amplification. The adapter mediated multiplexing of the invention is an alternative to conventional multiplexing which gives improved results in certain cases. Of the foregoing publications, only EPO 0 364 255 and Mueller and Wold address the problem of simultaneously amplifying multiple target sequences. Both teach simultaneous amplification for PCR, which in part due to its temperature cycling provides significantly different reaction conditions as compared to isothermal amplifications such as SDA. Although certain of the foregoing publications describe appending defined sequences to either end of a fragment prior to amplification, the addition of the defined end and amplification are performed in separate reactions. Further, the present invention for the first time provides methods for simultaneously amplifying multiple target sequences by SDA without the necessity of providing separate specific primers for each target. The inventive methods are particularly advantageous in that addition of defined adapter sequences to the ends of the target sequences and the amplification reaction occur in a single reaction mix and appear as a single step to the practitioner.

SUMMARY OF THE INVENTION

According to the present invention, a single primer or pair of primers can be used to coamplify multiple target nucleic acid sequences. Defined adapter sequences are appended to the ends of the target sequences within the context of the amplification reaction so that no additional manipulations are involved to append the adapter sequences. That is, the target sequences with the appended adapter sequences need not be isolated prior to amplification. In one embodiment for coamplifying two target sequences, a sequence corresponding to a terminal segment from one of the two strands of the first target sequence is appended to the 5' end of one of the two strands of the second target sequence and a sequence corresponding to a terminal segment from one of the two strands of the second target sequence is appended to the 5' end of one of the two strands of the first target sequence. Amplification of the two modified targets then requires only a single pair of amplification primers. One amplification primer of the pair hybridizes to a sequence corresponding to the first target and the other amplification primer of the pair hybridizes to a sequence corresponding to the second target. Alternatively, a single pair of sequences from one target may be appended to the 5' and 3' ends of each strand of any number of targets. In another embodiment, two arbitrary "universal" adapter sequences may be appended to the ends of any number of targets. All such modified target sequences may then be amplified using a single pair of "universal" primers which hybridize to the appended end-sequences.

The methods of the invention are particularly advantageous for SDA, as the required number of amplification primer pairs containing restriction enzyme recognition sites is reduced from one pair/target to a single pair, or, alternatively, to a single amplification primer. With fewer amplification primer pairs, the formation of primer dimers and nonspecific background amplification are reduced. The inventive methods also allow a reduction in the concentration of primers, as the adapter primer which contains the defined sequence is present at much lower concentration than the amplification primer it replaces.

DETAILED DESCRIPTION OF THE INVENTION

The present invention provides methods for simultaneous amplification of multiple target sequences by primer extension, particularly by SDA (multiplex SDA). The methods use a single pair of amplification primers or a single SDA amplification primer to coamplify the multiple target sequences. This is accomplished by appending a defined adapter sequence to the targets and amplifying by primer extension. The inventive methods are referred to herein as "adapter-mediated multiplexing." This is in contrast to "conventional multiplexing" in which multiple pairs of target-specific primers are used to coamplify the multiple targets without addition of adapter sequences.

The following terms are defined herein as follows:

An amplification primer is a primer for amplification of a target sequence by primer extension. For SDA, the 3' end of the amplification primer (the target binding sequence) hybridizes at the 3' end of the target sequence and comprises a recognition site for a restriction enzyme near its 5' end. The recognition site is for a restriction enzyme which will nick one strand of a DNA duplex when the recognition site is hemimodified, as described by Walker, et al. (1992. *PNAS* 89, 392–396) and in U.S. Ser. No. 07/819,358, filed Jan. 9, 1992 (the disclosure of which is hereby incorporated by reference). A hemimodified recognition site is a double stranded recognition site for a restriction enzyme in which one strand contains at least one derivatized nucleotide which prevents cutting of that strand by the restriction enzyme. The other strand of the hemimodified recognition site does not contain derivatized nucleotides and is nicked by the restriction enzyme. The preferred hemimodified recognition sites are hemiphosphorothioated recognition sites for the restriction enzymes HincII, HindII, AvaI, NciI and Fnu4HI. For the majority of the SDA reaction, the amplification primer is responsible for exponential amplification of the target sequence.

An adapter primer has a sequence at its 3' end (the target binding sequence) which hybridizes to the target sequence. At the 5' end of the adapter primer is an adapter sequence. The adapter sequence may be a sequence which is substantially identical to the 3' end of one of the amplification primers or it may be any defined sequence for which amplification primers with complementary target binding sequences can be prepared.

A bumper primer is a primer which anneals to a target sequence upstream of either an adapter or amplification primer, such that extension of the bumper primer displaces the downstream primer and its extension product. Extension of bumper primers is one method for displacing the extension products of adapter and amplification primers, but heating is also suitable.

Identical sequences will hybridize to the same complementary nucleotide sequence. Substantially identical sequences are sufficiently similar in their nucleotide sequence that they also hybridize to the same nucleotide sequence.

The terms target or target sequence refer to nucleic acid sequences to be amplified. These include the original nucleic acid sequence to be amplified and its complementary second strand (prior to addition of adapter sequences), either strand of an adapter-modified copy of the original sequence as described herein, and either strand of a copy of the original sequence which is an intermediate product of the reactions in which adapter sequences are appended to the original sequence.

In the adapter-mediated multiplexing of the invention, adapter sequences are appended to the ends of target sequences by means of adapter primers and a series of extension and strand displacement steps as described below. An adapter primer is an oligonudeotide comprised of (i) an adapter sequence at its 5' end and (ii) a target binding sequence at its 3' end. The 5' adapter sequence may be any sequence for which a suitable amplification primer can be prepared. The adapter sequence may be arbitrary or it may correspond to a segment of one of the target sequences. The adapter and target binding regions of an adapter primer may be contiguous, or they may be separated by a segment of unrelated sequence. Different adapter palmers may or may not have common 5' adapter sequences (as described below), but they will generally have different 3' target binding sequences to achieve hybridization to the various targets. A unique adapter primer will therefore usually be required for each target end to be modified by attachment of an adapter sequence. One or both ends of a target sequence may be modified by the attachment of adapter sequences. When both ends of a target sequence are modified the two appended sequences may be identical or they may be different, depending on the choice of adapter primers.

By way of example, the following detailed description of the invention is directed to primer extension amplification by SDA. It will be apparent to one skilled in the art that these methods are readily applicable to any method for DNA amplification which is based on extension of primers by polymerase. These include, for example, the 3SR and PCR amplification methods discussed above. To adapt the inventive methods to these amplification reactions, the SDA amplification primers would be replaced with amplification primers appropriate for the selected primer extension amplification reaction, as is known in the art. The adapter primers would be essentially unchanged regardless of the primer extension amplification method selected.

Figure 1:
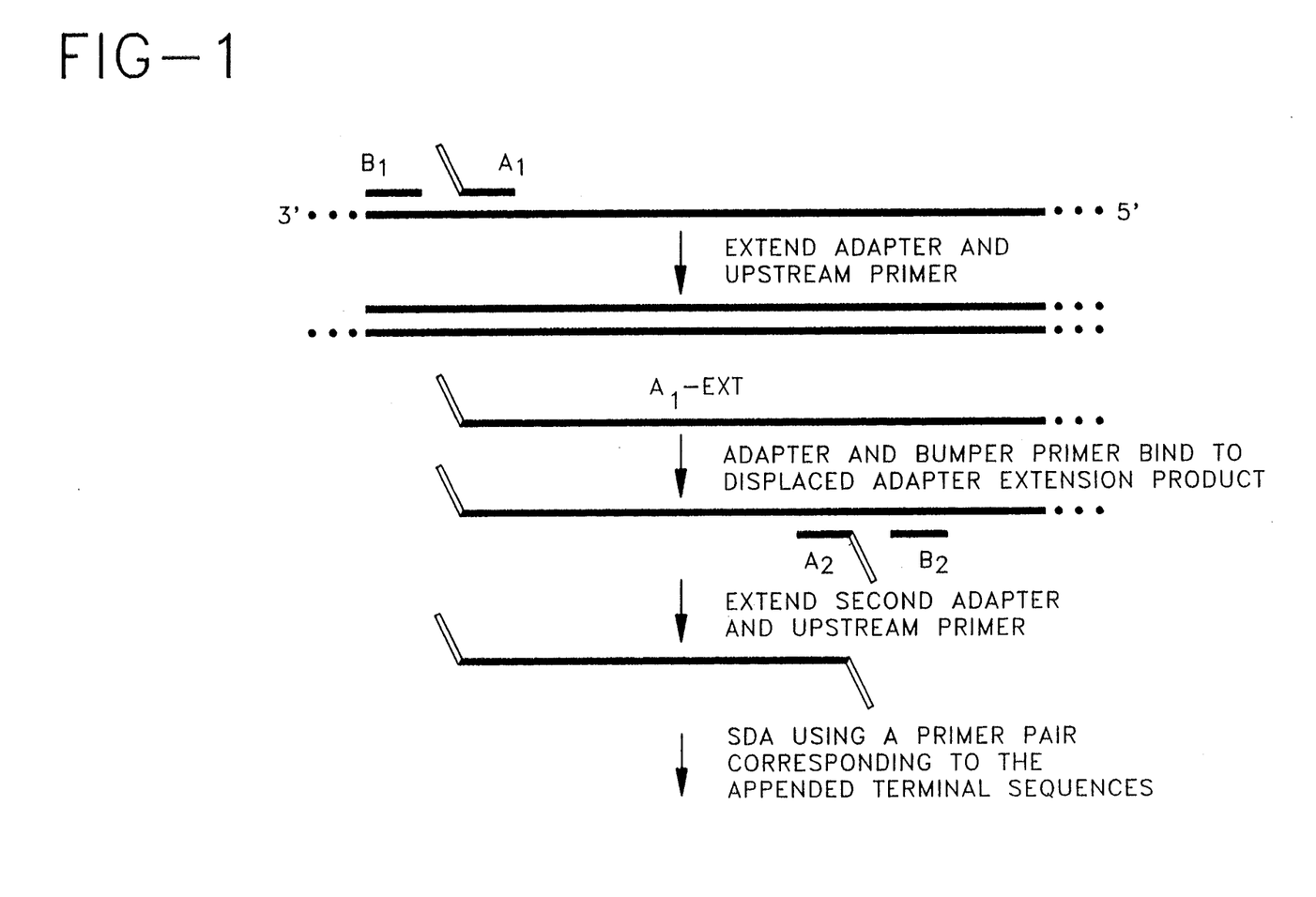
FIG. 1 is a diagram illustrating the method of the invention for appending adapter sequences to both ends of a target sequence.

FIG. 1 illustrates a preferred method for modifying both ends of a target sequence by attachment of defined adapter sequences. A first adapter primer ($A_1$) is hybridized to a target DNA at the 3' end of the target DNA sequence. The target binding sequence of $A_1$ is at the 3' end and the selected adapter sequence is at the 5' end. A first bumper primer ($B_1$) as described by Walker, et al. (1992. *Nuc. Acids Res.* 20, 1691–1696) is hybridized to the target DNA upstream of the first adapter primer. The first adapter primer and first bumper primer are extended with polymerase. Extension of the upstream bumper primer displaces the extension product of the first adapter primer ($A_1$-ext), which includes the adapter sequence at its 5' end but is otherwise complementary to the original target DNA sequence. The target binding sequence (3' end) of a second adapter primer ($A_2$) is then hybridized to the first adapter extension product ($A_1$-ext) at a position corresponding to the 3' end of the sequence complementary to the original target sequence. The 5' end of $A_2$ comprises a second adapter sequence, which may be the same as the $A_1$ adapter sequence or different from it. Polymerization and displacement by extension of a second bumper primer ($B_2$) as before produces a single stranded copy of the original target sequence with adapter sequences appended to the 5' and 3' ends. Specifically, the 5' end of this modified target derives directly from the second adapter primer, while the 3' end of the modified target (which comes indirectly from the first adapter) is comprised of a sequence complementary to the first adapter sequence.

For brevity, FIG. 1 depicts target generation from only one of the two complementary target strands normally present in a sample. Generation of modified targets from the second strand is analogous to generation of modified targets from the first strand as shown in FIG. 1, except that the order of binding and extension of the first and second adapter primers is reversed. That is, $A_2$ is bound and extended first and $A_1$ binds to the extension product of $A_2$ and is extended. Binding and extension of the first and second bumper primers is similarly reversed. The net result of the corresponding extension and displacement reactions for the second strand is a modified target fragment which has a sequence identical to the first adapter sequence at the 5' end and a sequence complementary to the second adapter sequence at the 3' end. All strands of the target sequences, terminally modified with adapter sequences, can then be amplified exponentially by amplification primers whose target binding sequences (at the 3' end of the primer) are substantially identical to the first and second adapter sequences at the 5' ends of the adapter primers used to generate the modified targets.

The process illustrated in FIG. 1 can be used to modify multiple target sequences simultaneously within a single reaction mixture provided the mixture contains an appropriate adapter primer for each target end to be modified. The various adapter primers may be designed so that all modified target sequences generated contain the same pair of appended sequences. All terminally modified target strands may then be amplified by the same pair of amplification primers. Alternatively, if all adapter primers contain the same 5' adapter sequence only a single amplification primer is needed to amplify all modified target strands.

Figure 2:
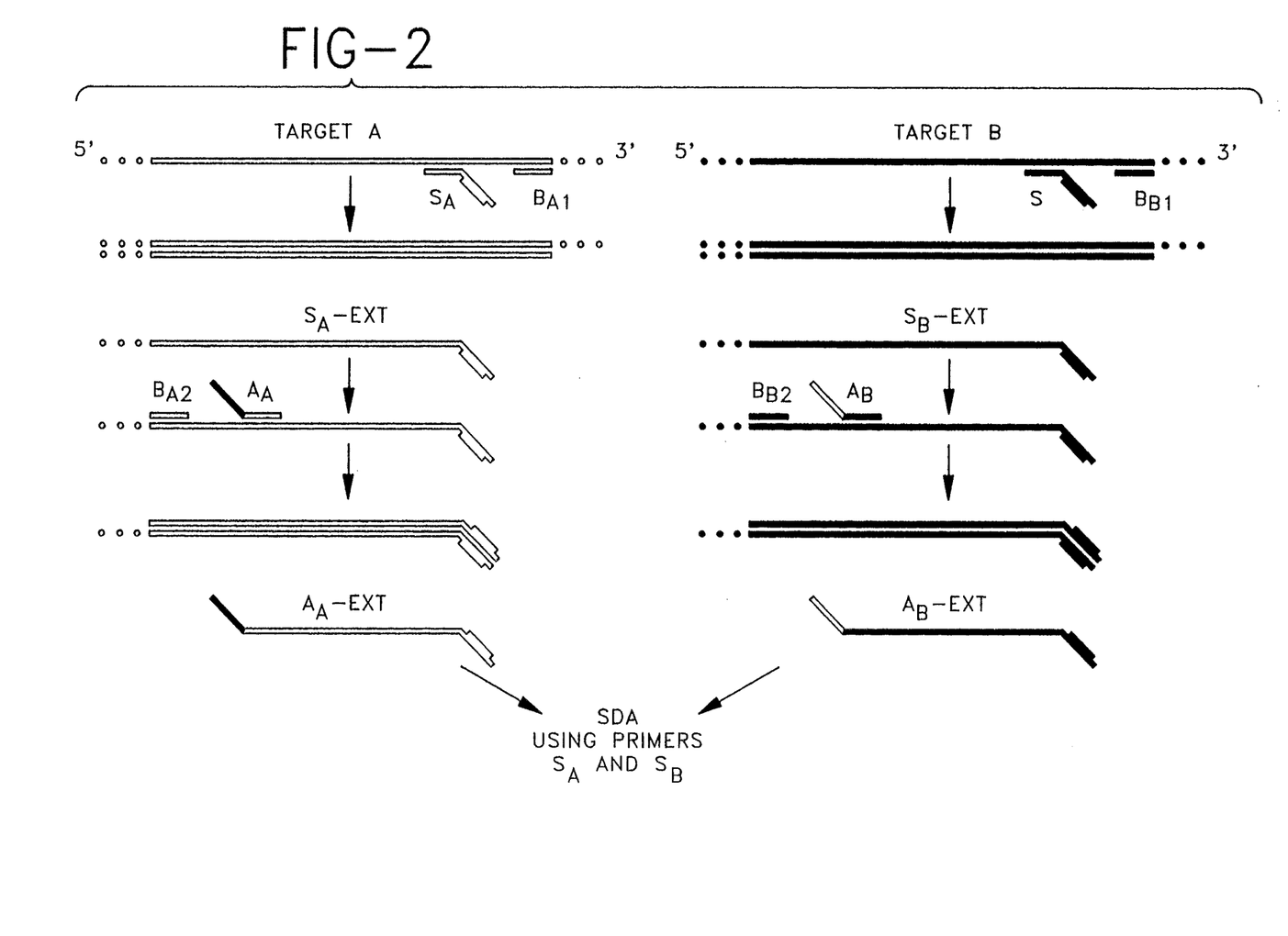
FIG. 2 is a diagram illustrating the method of the invention for coamplification of two target sequences.

FIG. 2 illustrates an alternative embodiment of the present invention in which two target sequences are co-amplified using a single pair of amplification primers. Again, modification of only one strand of each target sequence is illustrated for clarity. In this embodiment, one end of each target strand is modified by appending to it a sequence substantially identical to a terminal segment of the other target. The other end of each target strand remains unmodified and retains its original complementarity to one member of the amplification primer pair. As detailed below, the resulting modified targets can then both be amplified by a single pair of amplification primers, one member of the pair being complementary to one of the two original target sequences and the other member of the pair being complementary to the other of the two original target sequences. For the first target (A), an A-specific amplification primer ($S_A$) is hybridized to the 3' end of the target sequence and extended with polymerase. The nicking enzyme recognition site of the amplification primer is depicted in FIG. 2 as a raised portion of the primer. The resulting extension product is displaced by extension of a bumper primer ($B_{A1}$) which hybridizes to the target upstream from $S_A$. The displaced $S_A$ extension product ($S_A$-ext) is hybridized to an adapter primer ($A_A$) which binds to $S_A$-ext at the 3' end of the complement of the original target sequence. The 5' end of $A_A$ comprises the adapter sequence (solid portion), which is substantially identical to the target binding sequence at the 3' end of $S_B$, an amplification primer which specifically binds to the second target (B). Extension of $A_A$ and displacement of the $A_A$ extension product ($A_A$-ext) produces a single stranded copy of the A target sequence with a nicking enzyme recognition site and the A target sequence at its 3' end and the $S_B$ target binding sequence at its 5' end.

The second target (B) is treated similarly, first binding and extending a B-specific amplification primer ($S_B$), then hybridizing an adapter primer ($A_B$) to the extension product ($S_B$-ext). $S_B$ hybridizes to B at a 3' terminal segment of B which is complementary to both the target binding sequence of $S_B$ and the adapter sequence of $A_A$. The 3' end of adapter primer $A_B$ hybridizes at the 3' end of the complement of the original target and the 5' end of $A_B$ (open portion) is substantially identical to the target binding sequence of $S_A$. Extension and displacement of the $A_B$ extension product ($A_B$-ext) produces a copy of the second target sequence with a nicking enzyme recognition site (raised portion) and the B target sequence at its 3' end and the $S_A$ target binding sequence at its 5' end. The two adapter-modified copies of the target sequences are amplifiable by SDA using only the $S_A$ and $S_B$ amplification primers already present in the reaction. To begin SDA, $A_A$-ext and $A_B$-ext hybridize to their respective amplification primers, which are extended to produce the complement of the modified strand (i.e., extension of $S_A$ on the A modified strand and extension of $S_B$ on the B modified strand), including the complement of the adapter sequence at the 3' end. After nicking and displacement, the amplification primer of the opposite target can then bind to the 3' end of this extension product (i.e., $S_B$ to the A-derived strand and $S_A$ to the B-derived strand) and is extended to produce a fragment with a nicking enzyme recognition site at each end. This fragment is amplified by conventional SDA as described by Walker, et al., supra.

The double stranded reaction products which are produced after displacement of $A_A$-ext and $A_B$-ext may also participate in a reaction loop which generates additional copies of $A_A$-ext and $A_B$-ext. Nicking the restriction enzyme recognition site of the bottom strand, extending with polymerase and displacing the bottom strand produces targets which are similar to $S_A$-ext and $S_B$-ext but with half of a restriction enzyme recognition site at the 5' end. The adapter primers can bind to these fragments as shown in FIG. 2 and can be extended and displaced to produce additional copies of $A_A$-ext and $A_B$-ext (also with half of a restriction enzyme recognition site at the 5' end) which enter the SDA reaction cycle as described above.

FIG. 2 depicts the generation of modified targets from only one of the two complementary strands normally present for each target sequence. Processes similar to those shown also originate from the second strand of each target. In the case of the second strand, however, the order of binding and extension of the primers is reversed. The adapter primers first bind directly to the target second strand and are extended on that template. After its subsequent displacement, the resulting adapter extension product hybridizes to the amplification primer, which is in turn extended and displaced to give a product containing the original second strand target sequence with a recognition site for a nicking restriction enzyme at its 5' end and a sequence complementary to the adapter sequence at its 3' end. This modified fragment enters conventional SDA amplification by binding and extension of the amplification primer specific for the opposite target (i.e., $S_B$ binds to the A-derived strand and $S_A$ binds to the B-derived strand), producing a fragment for each target second strand with a nicking enzyme recognition site at each end.

All of the reaction steps involved in appending the adapter sequences and amplifying the target may occur concurrently in a single reaction mixture. That is, once adapter sequences are appended to a target molecule, amplification of that target molecule can take place within the same reaction mixture prior to appending of the adapter sequences to any other target molecules present and without isolation of the modified target. Reaction conditions for the methods of the invention are essentially as described by Walker, et al., supra, for SDA, with some modifications. First, the initial reaction mix contains both the amplification primers and the adapter primers as well as the target DNA. In addition, the amplification primers are present in about 10-fold excess over the adapter primers. However, like conventional SDA, the nicking restriction enzyme and exo$^-$ klenow polymerase are added after heat denaturation of the target DNA and annealing of the primers. After denaturation of the target DNA, annealing of the primers and addition of polymerase, the processes of appending the adapter sequences and amplification proceed automatically in a single reaction mixture without further intervention by the practitioner. That is, after adapter sequences are appended, a modified target sequence automatically enters the SDA reaction cycle. If necessary, universal primers may be capped at the 3' end to prevent extension by polymerase and reduce background reactions resulting from formation of primer dimers.

EXAMPLE 1

Coamplification of two target sequences was compared using conventional multiplexing and adapter-mediated multiplexing. The first target was the IS6110 insertion element of *Mycobacterium tuberculosis* (target "A", Thierry, et al. 1990). The second target was the 16S ribosomal gene of *Mycobacterium tuberculosis* (target "B"). Conventional multiplexing employed a full set of four primers for each target sequence ($S_1$, $S_2$, $B_1$ and $B_2$ as described by Walker, et al., *Nuc. Acids Res.*, supra), i.e., a total of eight primers for the two target sequences. For adapter-mediated multiplexing, as illustrated in FIG. 2, one of the S primers for each target sequence was replaced with an adapter primer at a concentration 10-fold less than the concentration of the S primer it replaced.

SDA was performed generally as described by Walker, et al., *Nuc. Acids Res.*, supra. The final concentrations of components was 45 mM $K_iPO_4$, pH 7.5, 6 mM $MgCl_2$, 0.5 mM dUTP, 0.2 mM dGTP, 0.2 mM dCTP, 0.2 mM dATPαS, 0.1 mg/mL acetylated BSA, 12% (v/v) dimethylsulfoxide, 3% (v/v) glycerol (supplied by the stock solutions of exo⁻ klenow and HincII), 250 ng human placental DNA, 2.5 units exo⁻ klenow (United States Biochemical, Cleveland, Ohio), 150 units HincII (New England Biolabs, Beverly, Mass.), and 0, 50, 500 or 5,000 *Mycobacterium tuberculosis* genomes (molecules). For conventional multiplex amplification, the samples also contained the following primers: 500 nM of each of SEQ ID NO: 1 ($S_{2A}$), SEQ ID NO: 2 ($S_{1A}$), SEQ ID NO: 3 ($S_{1B}$) and SEQ ID NO: 4 ($S_{2B}$); 25 nM of each of SEQ ID NO: 5 ($B_{1A}$), SEQ ID NO: 6 ($B_{2A}$), SEQ ID NO: 7 (Bin) and SEQ ID NO: 8 ($B_{2B}$). For adapter-mediated multiplexing, the samples contained the following primers: 500 nM of each of SEQ ID NO: 2 ($S_A$ in FIG. 2) and SEQ ID NO: 3 ($S_B$ in FIG. 2); 50 nM of each of SEQ ID NO: 10 ($A_A$) and SEQ ID NO: 9 ($A_B$); 25 nM of each of SEQ ID NO: 5 ($B_{1A}$), SEQ ID NO: 6 ($B_2A$), SEQ ID NO: 7 ($B_{1B}$) and SEQ ID NO: 8 ($B_{2B}$).

Each 47 μL sample was assembled to contain all reagents except exo⁻ klenow and HincII using 10X concentrated stock solutions of each reagent. The $MgCl_2$ was added after addition and mixing of all other reagents (except exo⁻ klenow and HincII) to prevent precipitation which occurs when $K_iPO_4$, dimethylsulfoxide and $MgCl_2$ are mixed at concentrations considerably higher than 45 mM, 12% (v/v) and 6 mM, respectively. The samples were then heated for 2 min. in a boiling water bath to denature the *Mycobacterium tuberculosis* DNA. A precipitate was observed immediately after removal from the boiling water bath. Incubating for 2 min. at 40° C. and mixing on a vortex mixer redissolved the majority of the high temperature precipitate. Exo⁻ klenow (1 μL of a 2.5 units/μL stock solution) and HincII (2 μL of a 75 units/μL stock solution) were added and the samples were incubated for 2 hr. at 40° C.

Amplification products were detected by primer extension as described by Walker, et al., *Nuc. Acids Res.*, supra. A 5 μL aliquot of each sample was mixed with 5 μL of 45 mM $K_iPO_4$, pH 7.5, 6 mM $MgCl_2$, 0.5 mM duTP, 0.2 mM dGTP, 0.2 mM dCTP, 0.2 mM dATPα S, 0.1 mg/mL acetylated BSA and 2 μL of a 5'-³²P detector probe stock solution (50 mM Tris-HCl, pH 8, 10 mM $MgCl_2$, 1 μM 5'-³²P detector probe). The detector probe for target A was SEQ ID NO: 11 and the detector probe for target B was SEQ ID NO: 12. The 12 μL samples were then heated 1 min. in a boiling water bath. After incubating 2 min. at 37° C., 2 μL of 1 unit/μL of exo⁻ klenow were added and the samples were incubated for 15 min. at 37° C., followed by addition of 14 μL of 50% urea in 0.5X TBE.

Figure 3:
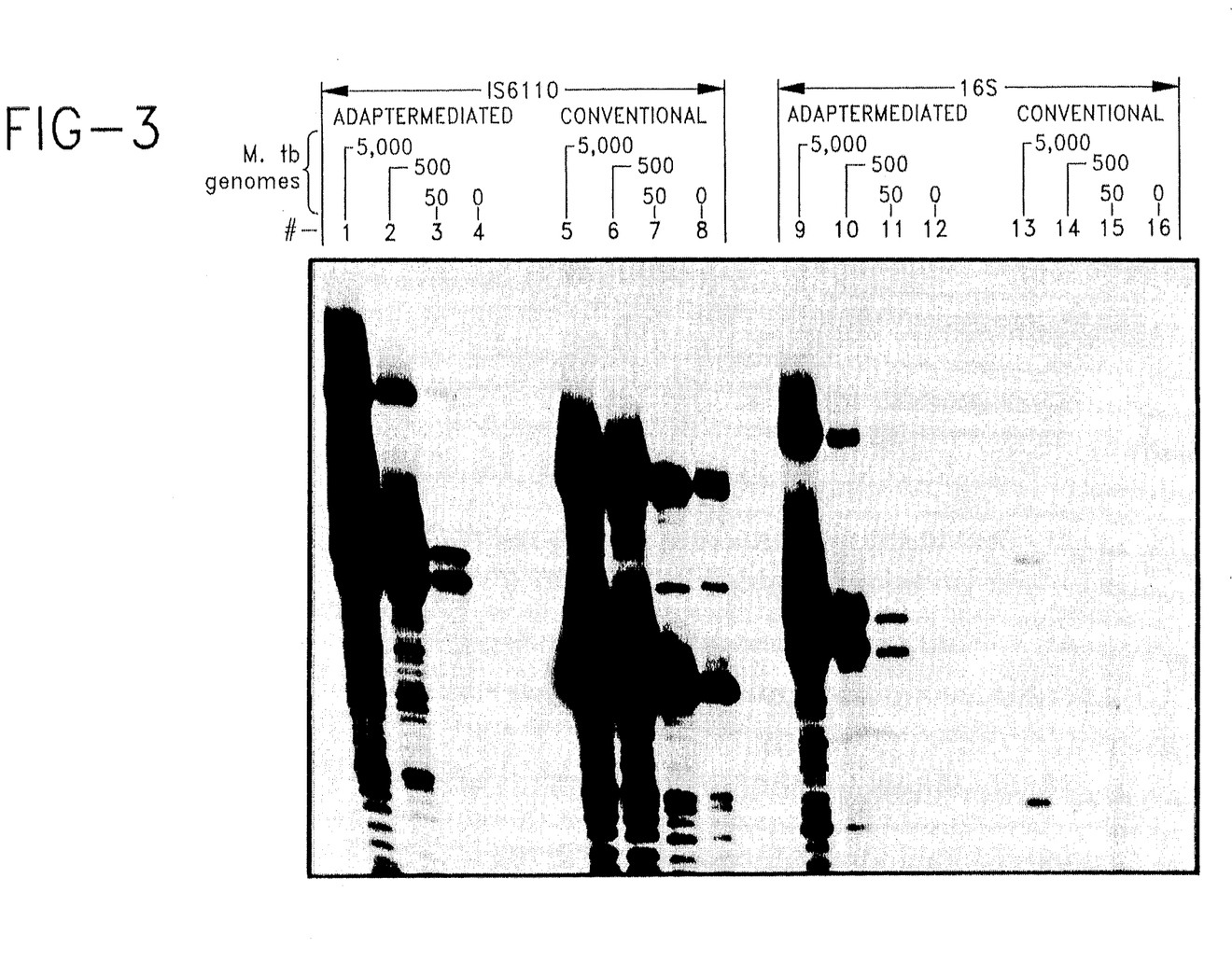
FIG. 3 is an autoradiograph showing the results of the experiment in Example 1.

Samples were heated for 1 min. at 95° C. and analyzed using 8% denaturing gel electrophoresis and autoradiography (Maniatis, et al. 1982. *Molecular Cloning: A Laboratory Manual* Cold Spring Harbor Laboratory, Cold Spring Harbor, N.Y.). The results are shown in FIG. 3. Lanes 1-8 represent SDA of the IS6110 sequence and lanes 9-16 represent SDA of the 16S gene sequence. Amplified IS6110 (target A) is indicated by extension of the SEQ ID NO: 11 detector probe to a 35- and 56-mer for conventional multiplexing (lanes 5-8) and a 44-, 47- and 68-mer for adapter-mediated multiplexing (lanes 1-4). Amplified 16S (target B) is indicated by extension of the SEQ ID NO: 12 detector probe to a 27-and 48-mer for conventional multiplexing (lanes 13-16) and a 39-, 42- and 63-mer for adapter-mediated multiplexing (lanes 9-12).

Only adapter-mediated multiplex amplification produced efficient amplification of both the IS6110 and 16S targets. For example, compare adapter-mediated amplification of 50 *Mycobacterium tuberculosis* genomes for both target sequences (lanes 3 and 11) with conventional multiplexing (lanes 7 and 15).

EXAMPLE 2

This example demonstrates using adapter-mediated multiplex SDA as illustrated in FIG. 2 to generate two targets which can be amplified using a single pair of SDA primers. The first target sequence (target "A") was the segment of the IS6110 insertion element of *Mycobacterium tuberculosis* used in Example 1. The second target sequence (target "B") was a sequence derived from *Mycobacterium avium* which is contained in plasmid pMAv29 (J. W. U. Fries, et al. 1990. *Molec. Cell. Probes* 4, 87–105). Plasmid pMAv29 was cut with the restriction endonuclease EcoRI to convert it to linear form prior to using it in the amplification reactions.

SDA was performed generally as described by Walker, et al., *Nuc. Acids Res.*, supra. The final concentrations of components in each 67 μL amplification reaction were: 48.3 mM $K_iPO_4$ (pH 7.5); 5.8 mM $MgCl_2$; 0.96 mM each dCTP, dGTP, dTTP, dATPαS; 0.09 mg/mL acetylated BSA; 3% (v/v) glycerol (supplied by the stock solutions of exo⁻ klenow and HincII); 0.85 ng/μL human placental DNA; 5.2 units exo⁻ klenow (United States Biochemical, Cleveland, Ohio); 154 units HincII (New England BioLabs, Beverly, Mass.); 0, 8, 83, 830 or 8300 copies of both *Mycobacterium tuberculosis* genomic DNA and plasmid pMAv29 DNA. In all reactions, the genomic *Mycobacterium tuberculosis* and plasmid pMAv29 DNA were present in equimolar ratios. The reaction mixtures also contained the following primers: 450 nM each SEQ ID NO: 13 ($S_A$ in FIG. 2) and SEQ ID NO: 14 ($S_B$); 45 nM each SEQ ID NO: 1 5 ($A_B$) and SEQ ID NO: 16 ($A_A$); 9 nM SEQ ID NO: 5 ($A_1$), SEQ ID NO: 6 ($BA_2$), SEQ ID NO: 17 ($B_{B1}$) and SEQ ID NO: 18 ($B_{B2}$).

All reaction components except HincII and exo⁻ klenow were assembled and the mixtures were heated to 95° C. for two minutes and then placed in a 37° C. water bath for 3-5 minutes. The enzymes HincII and exo⁻ klenow were then added, and the amplification mixture was incubated at 37° C. for two hours. After incubation the reactions were terminated by heating the samples to 95° C. for two minutes.

After cooling, the reaction mixtures were assayed for the presence of specific IS6110 or pMAv29 amplification products using 5'-$^{32}$P-labeled primer extension as in Example 1. A 15 μL aliquot of each sample was mixed with 2 μL of probe stock solution (containing 0.66 μM 5'-$^{32}$P-labeled detector probe, 16 mM Tris-HCl pH 8.0 and 3.3 mM MgCl$_2$). The detector probe for the IS6110 target was SEQ ID NO: 11, and the probe for the *Mycobacterium avium* sequence was SEQ ID NO: 19. The mixtures were heated to 95° C. for two minutes, and then placed in a 37° C. water bath. After 3-5 minutes, 3 μL of a solution containing the following components was added to each sample: 0.25 units/μL exo⁻ klenow; 9 mM Tris-HCl (pH 8.0); 1.8 mM MgCl$_2$; and 0.9 mM each of dCTP, dGTP, dTTP, dATPαS. The mixtures were incubated at 37° C. for 45 min. and the extension reactions terminated by addition of 30 μL of 50% urea in 0.5SX TBE. The samples were then heated to 95° C. for 2 minutes and 20 μL aliquots were analyzed by denaturing gel electrophoresis on a 10% polyacrylamide gel followed by autoradiography (Maniatis, et al., supra).

Figure 4:
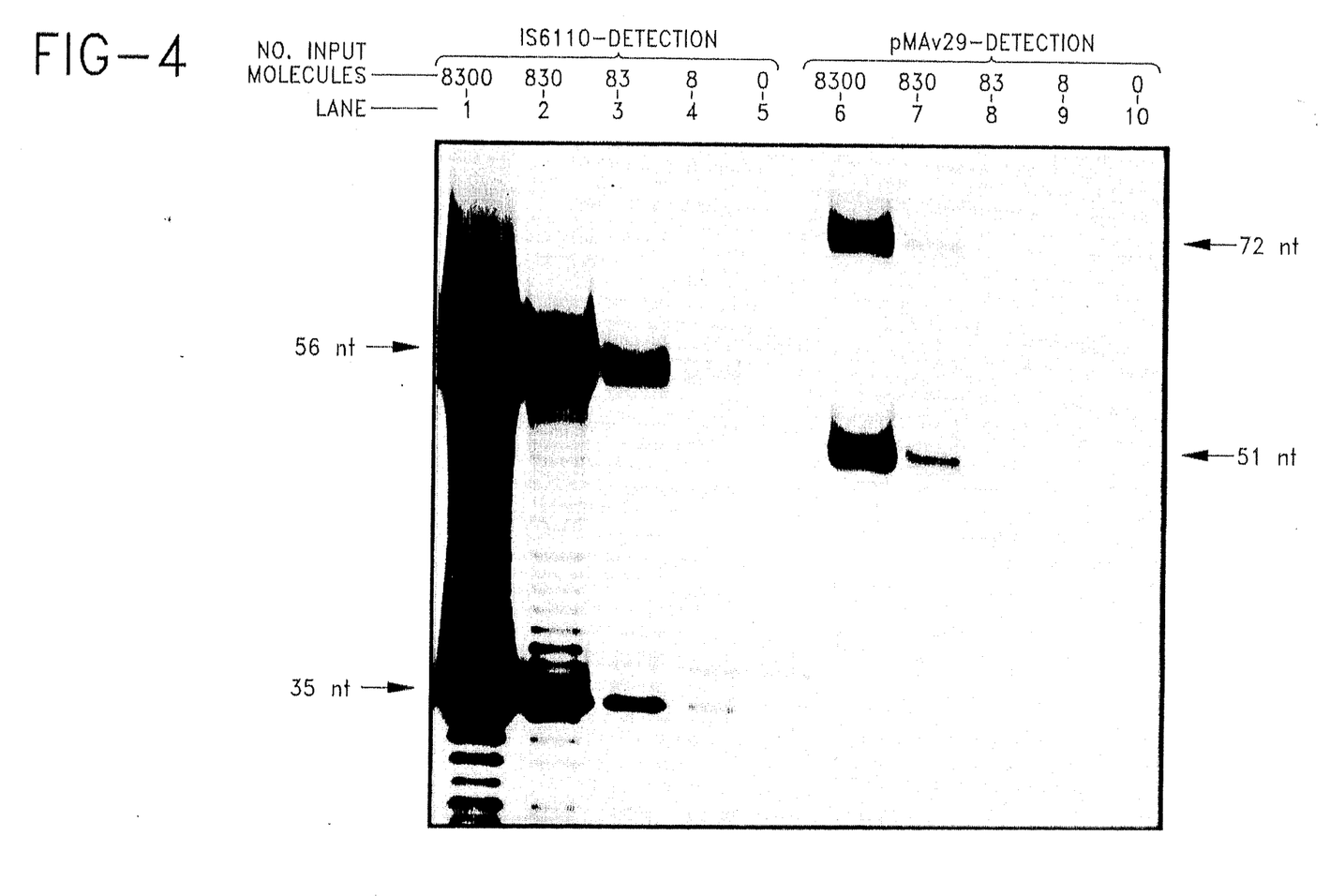
FIG. 4 is an autoradiograph showing the results of the experiment in Example 2.

The results of this analysis are shown in FIG. 4. The bands marked 35 and 56 nt in lanes 1-5 correspond to extension of the IS6110 specific detector primer SEQ ID NO: 11. These lanes show amplification of IS6110 targets to detectable levels from as few as 8 *Mycobacterium tuberculosis* genome copies using adapter-mediated multiplex SDA. In lanes 6-10, the bands marked 51 and 72 nt correspond to extension of the pMAv29 specific detector probe SEQ ID NO: 19. These lanes show amplification of as few as 83 input pMAv29 copies to detectable levels (see faint band in lane 8). Although the amplification reactions contained equimolar amounts of pMAv29 and genomic *Mycobacterium tuberculosis* DNA, the signal generated from each input genomic *Mycobacterium tuberculosis* DNA was substantially greater than that generated from each pMAv29 molecule because the *Mycobacterium tuberculosis* DNA contains about 10 copies of the IS6110 sequence per genome whereas pMAv29 contains only one target copy per plasmid molecule. Taken together, lanes 3 and 8 (which are separate analyses of the same amplification mixture) demonstrate successful adapter-mediated co-amplification of targets from as few as 83 input copies of pMAv29 and genomic *Mycobacterium tuberculosis* DNA. Both targets were also readily co-amplified when higher levels of input target DNA were present, as shown in lanes 1 and 6, and 2 and 7. Co-amplification of these same targets using conventional SDA multiplexing was about 10-fold less efficient than co-amplification using adapter-mediated multiplex SDA.

EXAMPLE 3

This example demonstrates co-amplification of a pMAv29 target sequence and a segment of the IS6110 insertion element with a single pair of amplification primers (SEQ ID NO: 1 and SEQ ID NO: 2) specific for IS6110, using the method illustrated in FIG. 1. Adapter primers SEQ ID NO: 20 and SEQ ID NO: 21 were used to generate copies of the pMAv29 target sequence containing IS6110 specific sequences at both ends. These terminally modified pMAv29 targets were then co-amplified with IS6110 using the IS6110 specific primers.

SDA was generally performed as described in the preceding Examples. The final concentrations of components in each 50 μL reaction were 50 mM K$_i$PO$_4$, pH 7.5; 6 mM MgCl$_2$; 1 mM each dTTP, dCTP, dGTP and dATPαS; 0.1 mg/mL acetylated BSA, 3% (v/v) 1-methyl-2-pyrrolidinone (NMP), 3% (v/v) glycerol (supplied by the stock solutions of exo⁻ klenow and HincII), 300 ng human placental DNA, 3.0 units exo⁻ klenow (United States Biochemical, Cleveland, Ohio), 150 units HincII (New England Biolabs, Beverly, Mass.); 1,000 copies of genomic *Mycobacterium tuberculosis* DNA and 100,000 copies of plasmid pMAv29 (prepared as described in Example 2). The reactions also contained the following primers: 500 nM each SEQ ID NO: 1 (S$_1$ in FIG. 1) and SEQ ID NO: 2 (S$_2$); 50 nM each SEQ ID NO: 20 (A$_1$) and SEQ ID NO: 21 (A$_2$) and 25 nM each SEQ ID NO: 18 (B$_1$) SEQ ID NO: 17 (B$_2$), SEQ ID NO: 5 and SEQ ID NO: 6. SEQ ID NO: 5 and SEQ ID NO: 6 served as bumper primers for generation of the IS6110 target as previously described. Adapter primers (SEQ ID NO: 20 and SEQ ID NO: 21) were withheld from control reactions labeled "Adapter—" in FIG. 5.

All reaction components except HincII and exo⁻ klenow were assembled and the mixtures were heated to 95° C. for two minutes and then placed in a 37° C. water bath for 3-5 minutes. After addition of the enzymes HincII and exo⁻ klenow, the amplification mixtures were incubated for 2 hours at 37° C. The amplification was terminated by heating the samples to 95° C. for two minutes.

After cooling, the reaction mixtures were assayed for the presence of amplification products by palmer extension as previously described. A 5 μL aliquot of each sample was mixed with (i) 10 μL of a solution containing 42.5 mM Tris-HCl (pH 8.0); 8.5 mM MgCl$_2$; 0.2 mM each of dCTP, dGTP, dTTP, dATPαS; and (ii) 3 μL of $^{32}$P-labeled detector probe stock solution (containing 0.66 μM 5'-$^{32}$P-labeled probe, 16 mM Tris-HCl (pH 8.0), and 3.3 mM MgCl$_2$). The detector probe for IS6110 target was SEQ ID NO: 11, and the pMAv29-specific probe was SEQ ID NO: 19. The mixtures were assembled and heated in a 95° C. water bath for two minutes. After incubation in a 37° C. water bath for 3-5 minutes, 3 μL of 0.34 units/μL exo⁻ klenow was added to each mixture and the samples were incubated at 37° C. for 15 min. The extension reactions were stopped by addition of 30 μL of 50% urea in 0.5SX TBE.

Figure 5:
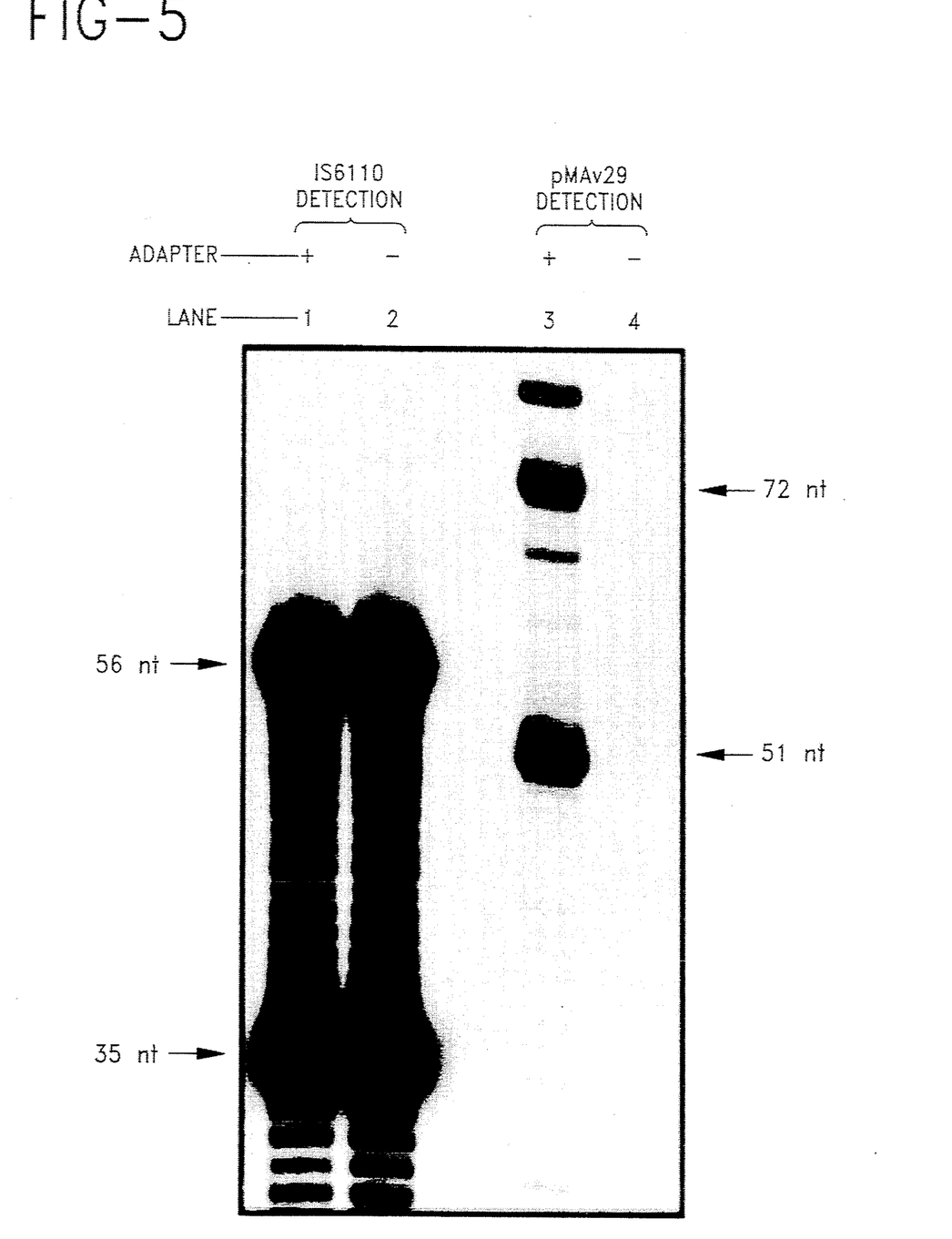
FIG. 5 is an autoradiograph showing the results of the experiment in Example 3.

Samples were heated to 95° C. for 2 minutes and 20 μL aliquots were analyzed by first separating $^{32}$P-labeled products by denaturing gel electrophoresis on a 10% polyacrylamide gel followed by autoradiography of the gel as previously described. FIG. 5 shows the autoradiogram of the gel. The bands marked 35 and 56 nt in lanes 1 and 2 correspond to extension of the IS6110-specific detector probe SEQ ID NO: 11. The bands marked 51 and 72 nt in lanes 3 and 4 correspond to extension of the pMAv29-specific detector probe SEQ ID NO: 19. Lanes 1 and 3 are separate analyses of the same (adapter-containing) amplification reaction, and lanes 2 and 4 are separate analyses of the same (adapter-free) amplification reaction.

The presence of strong IS6110-specific bands in both lanes 1 and 2 is expected, as both the "Adapter+" and "Adapter—" amplification reaction mixtures contained primers needed for amplification of the IS6110 target sequence. The strong product bands in the "Adapter-" lane indicates that the adapter sequences are not required for IS6110 amplification, and corresponding product bands of nearly equal intensity in the "Adapter+" lane show that the presence of adapters does not significantly interfere with IS6110 amplification.

In contrast, adapters are clearly required for amplification of the pMAv29 target sequence, as shown by the presence of pMAv29-specific product bands in lane 3 ("Adapter+") but not in lane 4 ("Adapter−"). This demonstrates adapter-mediated amplification of the pMAv29 target sequence with a pair of amplification primers specific for IS6110. In addition, lanes 1 and 3 taken together demonstrate successful co-amplification of the pMAv29 and IS6110 target sequences.

---

What is claimed is:

1. A method for simultaneously amplifying a first and a second target nucleic acid sequence by Strand Displacement Amplification (SDA) comprising:

a) hybridizing a first amplification primer to the 3' end of a first strand of the first target sequence, the first amplification primer comprising a 3' target binding sequence and a 5' recognition site for a restriction enzyme capable of nicking one strand of a double stranded hemimodified recognition site for the enzyme, extending the first amplification primer with polymerase to form a first extension product complementary to the first strand of the first target sequence, and displacing the first extension product;

b) hybridizing a first adapter primer to the first extension product at the 3' end of the complement of the first strand of the first target sequence, the 3' end of the first adapter primer comprising a target binding sequence which hybridizes to the first extension product and the 5' end of the first adapter primer comprising a sequence which is substantially identical to a 3' target binding sequence of a second amplification primer which hybridizes to a first strand of the second target sequence;

c) extending the first adapter primer with polymerase to form a second extension product and displacing the second extension product;

d) hybridizing the second amplification primer to the 3' end of the first strand of the second target sequence, the second amplification primer comprising the 3' target binding sequence and a 5' recognition site for a restriction enzyme which nicks one strand of a double stranded hemimodified restriction enzyme recognition site, extending the second amplification primer with polymerase to form a third extension product complementary to the first strand of the second target sequence, and displacing the third extension product;

e) hybridizing a second adapter primer to the third extension product at the 3' end of the complement of the first strand of the second target sequence, the 3' end of the second adapter primer comprising a target binding sequence which hybridizes to the third extension product and the 5' end of the second adapter primer comprising a sequence which is substantially identical to the target binding sequence of the first amplification primer;

f) extending the second adapter primer with polymerase to form a fourth extension product and displacing the fourth extension product, and;

g) simultaneously amplifying the second and fourth extension products in an SDA reaction using the first and second amplification primers.

2. The method according to claim 1 wherein the first, second, third and fourth extension products are displaced by extension of bumper primers.

3. The method according to claim 2 wherein the first and second amplification primers are present in approximately 10-fold excess over the first and second adapter primers.

4. The method according to claim 3 wherein the second and fourth extension products are amplified in an SDA reaction which employs a restriction enzyme selected from the group consisting of HincII, HindII, AvaI, NciI, and Fnu4HI for nicking the hemimodified restriction enzyme recognition site.

5. The method according to claim 4 wherein the IS6110 insertion element of *Mycobacterium tuberculosis* and the 16S ribosomal gene of *Mycobacterium tuberculosis* are simultaneously amplified.

6. The method of claim 1 wherein the first and second target sequences are double stranded, further comprising the steps of:

a) hybridizing the first adapter primer to the 3' end of a second strand of the first target sequence, extending the first adapter primer to form a fifth extension product complementary to the second strand of the first target sequence, and displacing the fifth extension product;

b) hybridizing the first amplification primer to the fifth extension product at the 3' end of the complement of the second strand of the first target sequence, extending the first amplification primer with polymerase to form a seventh extension product, and displacing the seventh extension product;

c) hybridizing the second adapter primer to the 3' end of a second strand of the second target sequence, extending the second adapter primer to form a sixth extension product complementary to the second strand of the second target sequence, and displacing the sixth extension product;

d) hybridizing the second amplification primer to the sixth extension product at the 3' end of the complement of the second strand of the second target sequence, extending the second amplification primer with polymerase to form an eighth extension product, and displacing the eighth extension product, and;

e) simultaneously amplifying the seventh and eight extension products in the SDA reaction using the first and second amplification primers.

7. A method for simultaneously amplifying a first and a second target nucleic acid sequence by Strand Displacement Amplification (SDA) comprising, in a reaction mix comprising adapter primers and amplification primers:

a) hybridizing a first adapter primer to the 3' end of the first target sequence, the 3' end of the adapter primer comprising a target binding sequence which hybridizes to the target sequence and the 5' end of the adapter primer comprising a first adapter sequence which is substantially identical to a 3' target binding sequence of a first amplification primer which hybridizes to a first strand of the second target sequence;

b) extending the first adapter primer with polymerase to produce a first extension product which is complementary to the first target sequence and displacing the first extension product;

c) hybridizing a second adapter primer to the 3' end of the first extension product at the 3' end of the complement of the first target sequence, the 3' end of the second adapter primer comprising a target binding sequence which hybridizes to the first extension product and the 5' end of the second adapter primer comprising a second adapter sequence which is substantially identical to a 3' target binding sequence of a second amplification primer which hybridizes to a second strand of the second target sequence;

d) extending the second adapter primer with polymerase to produce a second extension product, displacing the second extension product, and;

e) concurrently with production of the second extension product in the reaction mix, simultaneously amplifying the second extension product of the first target sequence and the second target sequence in an SDA reaction using the first and second amplification primers, the first and second amplification primers each further comprising a 5' recognition site for a restriction enzyme which nicks one strand of a hemimodified double stranded restriction enzyme recognition site.

8. The method according to claim 7 wherein the first and second adapter sequences are substantially identical and the second extension product of the first target sequence and the second target sequence are amplified using a single amplification primer.

9. The method according to claim 7 wherein the first and second extension products are displaced by extension of bumper primers.

10. The method according to claim 9 wherein the amplification primers first and second are present in approximately 10-fold excess over the first and second adapter primers.

11. The method according to claim 10 wherein the IS6110 insertion element of *Mycobacterium tuberculosis* and the 16S ribosomal gene of *Mycobacterium tuberculosis* are amplified.

12. The method according to claim 10 wherein the IS6110 insertion element of *Mycobacterium tuberculosis* and a target sequence from *Mycobacterium avium* are amplified.

13. The method according to claim 7 wherein the second extension product is amplified in an SDA reaction which employs a restriction enzyme selected from the group consisting of HincII, HindII, AvaI, NciI, and Fnu4HI for nicking the hemimodified restriction enzyme recognition site.

14. The method according to claim 7 further comprising the steps of:

a) hybridizing the second adapter primer to the 3' end of a second strand of the first target sequence, extending the second adapter primer to form a third extension product complementary to the second strand of the first target sequence, and displacing the third extension product;

b) hybridizing the first adapter primer to the third extension product at the 3' end of the complement of the first target sequence, extending the first adapter primer to form a fourth extension product, and displacing the fourth extension product, and;

c) concurrently with formation of the fourth extension product in the reaction mix, simultaneously amplifying the fourth extension product of the first target sequence and the second target sequence in the SDA reaction using the first and second amplification primers.

15. A method for simultaneously amplifying a first and a second target nucleic acid sequence in a primer extension amplification reaction comprising:

a) hybridizing a first amplification primer to the 3' end of the first target sequence, the first amplification primer comprising a 3' target binding sequence, extending the first amplification primer with polymerase to form a first extension product complementary to the first target sequence, and displacing the first extension product;

b) hybridizing a first adapter primer to the first extension product at the 3' end of the complement of the first target sequence, the 3' end of the first adapter primer comprising a target binding sequence which hybridizes to the first extension product and the 5' end of the first adapter primer being substantially identical to a 3' target binding sequence of a second amplification primer which hybridizes to the second target sequence;

c) extending the first adapter primer with polymerase to form a second extension product and displacing the second extension product;

d) hybridizing the 3' target binding sequence of the second amplification primer to the 3' end of the second target sequence, extending the second amplification primer with polymerase to form a third extension product complementary to the second target sequence, and displacing the third extension product;

e) hybridizing a second adapter primer to the third extension product at the 3' end of the complement of the second target sequence, the 3' end of the second adapter primer comprising a target binding sequence which hybridizes to the third extension product and the 5' end of the second adapter primer being substantially identical to the target binding sequence of the first amplification primer;

f) extending the second adapter primer with polymerase to form a fourth extension product and displacing the fourth extension product, and;

g) simultaneously amplifying the second and fourth extension products in a primer extension amplification reaction using the first and second amplification primers.

16. A method for simultaneously amplifying a first and second target nucleic acid sequence in a primer extension amplification reaction comprising, in a reaction mix comprising adapter primers and amplification primers:

a) hybridizing a first adapter primer to the 3' end of the first target sequence, the 3' end of the adapter primer comprising a target binding sequence which hybridizes to the target sequence and the 5' end of the adapter primer comprising a first adapter sequence which is substantially identical to a 3' target binding sequence of a first amplification primer which hybridizes to a first strand of the second target sequence;

b) extending the first adapter primer with polymerase to produce a first extension product which is complementary to the first target sequence and displacing the first extension product;

c) hybridizing a second adapter primer to the first extension product at the 3' end of the complement of the first target sequence, the 3' end of the second adapter primer comprising a target binding sequence which hybridizes to the first extension product and the 5' end of the second adapter primer comprising a second adapter sequence which is substantially identical to a 3' target binding sequence of a second amplification primer which hybridizes to a second strand of the second target sequence;

d) extending the second adapter primer with polymerase to produce a second extension product, displacing the second extension products, and;

e) concurrently with production of the second extension products in the reaction mix, simultaneously amplifying the second extension product of the first target and the second target sequence in a primer extension amplification reaction using the first and second target sequence in a primer extension amplification reaction using the first and second amplification primers.

17. The method according to any one of claims 7 or 16 further comprising appending adapter sequences to a third target nucleic acid sequence according to steps (a) through (d) and simultaneously amplifying the first, second and third target sequences using the first and second amplification primers.

* * * * *

UNITED STATES PATENT AND TRADEMARK OFFICE
CERTIFICATE OF CORRECTION

PATENT NO. : 5,422,252

DATED : June 6, 1995

INVENTOR(S): George T. Walker, James G. Nadeau and Michael C. Little

It is certified that error appears in the above-identified patent and that said Letters Patent is hereby corrected as shown below:

In the drawings, Fig. 2, in the reaction illustrated for "Target B", the label "S" should read --$S_B$--.

Signed and Sealed this

Eighteenth Day of June, 1996

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:1:

TTGAAGTAAC CGACTATTGT TGACACTGAG ATCCCCT                                37

( 2 ) INFORMATION FOR SEQ ID NO:2:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:2:

TTGAATAGTC GGTTACTTGT TGACGGCGTA CTCGACC                                37

( 2 ) INFORMATION FOR SEQ ID NO:3:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:3:

TTCTATAGTC GGTTACTTGT TGACGTCGCG TTGTTC                                 36

( 2 ) INFORMATION FOR SEQ ID NO:4:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:4:

TTCCATAGTC CCAATCTTGT TGACGCTCAC AGTTA                                  35

( 2 ) INFORMATION FOR SEQ ID NO:5:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:5:

TGGACCCGCC AAC                                                                           13

( 2 ) INFORMATION FOR SEQ ID NO:6:

( i ) SEQUENCE CHARACTERISTICS:
  ( A ) LENGTH: 13 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:6:

CGCTGAACCG GAT 13

( 2 ) INFORMATION FOR SEQ ID NO:7:

( i ) SEQUENCE CHARACTERISTICS:
    ( A ) LENGTH: 13 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:7:

CGGAATTACT GGG 13

( 2 ) INFORMATION FOR SEQ ID NO:8:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:8:

AGTCTGCCCG TATC 14

( 2 ) INFORMATION FOR SEQ ID NO:9:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:9:

GGCGTACTCG ACCACGCTCA CAGTTA 26

( 2 ) INFORMATION FOR SEQ ID NO:10:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:10:

GTCGCGTTGT TCACTGAGAT CCCCT 25

( 2 ) INFORMATION FOR SEQ ID NO:11:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:11:

CGTTATCCAC CATAC 15

( 2 ) INFORMATION FOR SEQ ID NO:12:

( i ) SEQUENCE CHARACTERISTICS:
    ( A ) LENGTH: 13 base pairs
    ( B ) TYPE: nucleic acid ( C ) STRANDEDNESS: single
        ( D ) TOPOLOGY: linear ( x i ) SEQUENCE DESCRIPTION: SEQ ID NO:12:

AAATCTCACG GCT                                                                        1 3

( 2 ) INFORMATION FOR SEQ ID NO:13:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

GCATTATAGT ACCTGTCTGT TGACACTGAG ATCCCCT                                               3 7

( 2 ) INFORMATION FOR SEQ ID NO:14:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

TTGAATAGTA GGTAAGTTGT TGACACTTGT AAGAGCC                                               3 7

( 2 ) INFORMATION FOR SEQ ID NO:15:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

GACACTGAGA TCCCCTTGCG AGTGGGAAC                                                        2 9

( 2 ) INFORMATION FOR SEQ ID NO:16:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

GACACTTGTA AGAGCCAGGC GTACTCGACC                                                       3 0

( 2 ) INFORMATION FOR SEQ ID NO:17:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

TCCTCGGGCT CCA                                                                         1 3

( 2 ) INFORMATION FOR SEQ ID NO:18:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

```
TGGCCAAACT GTG                                                                        13
```

( 2 ) INFORMATION FOR SEQ ID NO:19:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:19:

```
CGCAAGGTTT TTGGAG                                                                     16
```

( 2 ) INFORMATION FOR SEQ ID NO:20:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:20:

```
GACACTGAGA TCCCCTTGCG AGTGGGAAC                                                       29
```

( 2 ) INFORMATION FOR SEQ ID NO:21:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:21:

```
GACGGCGTAC TCGACCACTT GTAAGAGCC                                                       29
```

( 2 ) INFORMATION FOR SEQ ID NO:22:

( i ) SEQUENCE CHARACTERISTICS:
        ( A ) LENGTH: 97 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:22:

```
TTGCCAAACT GTGGGCGCAG GCCTGCGAGT GGGAACCGGT GACTCCAAAA ACCTTGCGGC                     60
TCTTACAAGT CGGTGGCGCC AAGCTGGAGC CCGAGGA                                              97
```